United States Patent [19]

Tanouchi et al.

[11] Patent Number: 4,831,045
[45] Date of Patent: May 16, 1989

[54] RHODANINE DERIVATIVES, PROCESS FOR THEIR PREPARATION, AND ALDOSE REDUCTASE INHIBITOR CONTAINING THE RHODANINE DERIVATIVES AS ACTIVE INGREDIENT

[75] Inventors: Tadao Tanouchi, Takatsuki; Masanori Kawamura, Ibaraki; Akio Ajima, Osaka; Tetsuya Mohri, Takatsuki; Masaki Hayashi, Takatsuki; Hiroshi Terashima, Takatsuki; Fumio Hirata, Suita; Takeshi Morimura, Otsu, all of Japan

[73] Assignee: Ono Pharmaceutical Co., Ltd., Osaka, Japan

[21] Appl. No.: 96,091

[22] Filed: Sep. 10, 1987

Related U.S. Application Data

[62] Division of Ser. No. 591,753, Mar. 21, 1984, abandoned, Division of Ser. No. 292,076, Aug. 12, 1981, Pat. No. 4,464,382.

[30] Foreign Application Priority Data

Aug. 22, 1980 [JP] Japan .................. 55-115641

[51] Int. Cl.⁴ .................. C07D 417/06; A61K 31/425
[52] U.S. Cl. .................................... 514/369; 514/342; 546/280; 548/183
[58] Field of Search ............... 548/183; 546/280; 514/369, 342

[56] References Cited

FOREIGN PATENT DOCUMENTS 759323 10/1956 United Kingdom .............. 548/183
941552 11/1963 United Kingdom .............. 548/183
1224546 3/1971 United Kingdom .............. 548/183

OTHER PUBLICATIONS

Chemical Abstracts 66, 105907s (1967).
Chemical Abstracts 59, 8719h (1963).
Chemical Abstracts 55, 23502z (1961).
Chemical Abstracts 55, 24751g (1961).
Chemical Abstracts 89, 10933e (1978).
Chemical Abstracts 93, 213291c (1980).

*Primary Examiner*—Robert Gerstl
*Attorney, Agent, or Firm*—Sughrue, Mion, Zinn, Macpeak, and Seas

[57] ABSTRACT

The rhodanine derivatives of the general formula:

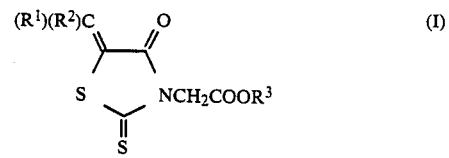

[wherein (I) $R^1$ and $R^2$ are taken together to represent a tetramethylene or pentamethylene group; (II) $R^1$ represents a hydrogen atom, and $R^2$ represents (1) a cycloalkyl or cycloalkenyl group of 4–7 carbon atoms which is unsubstituted or substituted by at least one alkyl group of 1–4 carbon atoms, (2) an anthryl or naphthyl group, (3) a phenyl group which is unsubstituted or substituted by at least one of (a) halogen atom, (b) trifluoromethyl group, (c) hydroxyl group, (d) nitro group, (e) carboxyl group, (f) amino group which may be substituted by alkyl group(s) of 1–4 carbon atoms, (g) alkyl, alkoxy or alkylthio group of 1–5 carbon atoms, (h) phenyl group, (i) heterocyclic group containing at least one of nitrogen, oxygen and sulfur atoms which is unsubstituted or substituted by at least one of the above-described substituents (a) to (h), and (j) alkyl group of 1–4 carbon atoms which is substituted by at least one of the above-described substituents (c), (h) and (i), (4) a heterocyclic group containing at least one of nitrogen, oxygen and sulfur atoms which is unsubstituted or substituted by at least one of oxo group and the above-described substituents (a) to (h) and (j), or (5) a

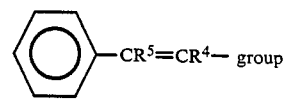

(wherein $R^4$ represents a hydrogen atom, a halogen atom, phenyl group or an alkyl group of 1–5 carbon atoms; and $R^5$ represents a hydrogen atom, a phenyl group or an alkyl group of 1–5 carbon atoms) or

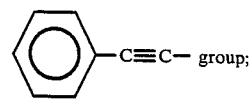

or (III) $R^1$ and $R^2$, which may be the same or different with each other, each represents a phenyl group which is unsubstituted or substituted by at least one of the above-described substituents (a) to (j); and $R^3$ represents a hydrogen atom, an alkyl group of 1–12 carbon atoms, an aralkyl group of 7–13 carbon atoms, a cycloalkyl or cycloalkenyl group of 4–7 carbon atoms which is unsubstituted or substituted by at least one alkyl group of 1–4 carbon atoms, or a phenyl group which is unsubstituted or substituted by at least one of the above-described substituents (a) to (j)] and, when $R^3$ represents a hydrogen atom, non-toxic salts of the acids possess a strong inhibitory activity on aldose reductase, and are useful for the prevention and treatment of nerve disturbances such as neuralgia, retinopathy, diabetic cataract and renal disturbances such as tubular nephropathy.

17 Claims, No Drawings

RHODANINE DERIVATIVES, PROCESS FOR THEIR PREPARATION, AND ALDOSE REDUCTASE INHIBITOR CONTAINING THE RHODANINE DERIVATIVES AS ACTIVE INGREDIENT

This is division of application Ser. No. 591,753, filed 3/21/84, which is a divisional of application Ser. No. 292,076 filed 8/12/81 U.S. Pat. No. 4,464,382.

This invention relates to novel rhodanine derivatives, process for their preparation and an aldose reductase inhibitor containing the rhodanine derivative as an active ingredient.

Hitherto, various compounds have been proposed for treating diabetes resulting from an increased blood sugar level due to deficient insulin secreted from pancreas. However, there are not so many compounds which are sufficiently satisfactory as drugs for the prevention or treatment of complications of chronic diabetes, particularly those ascribed to an aldose reductase such as retinopathy, diabetic cataract, nerve disturbances and renal disorders. An aldose reductase is an enzyme which reduces an aldose in human beings or other animals, for example, glucose or galactose, into the corresponding polyol, for example, sorbitol or galactitol. The sorbitol and galactitol produced by the action of this enzyme are accumulated in the crystalline lenses, the peripheral nerves, the kidney, etc. of diabetics and galactosemiacs thus causing the above-described complications [cf. Jap. J. Opthalmol., 20, 399 (1976), Int. Congr. Ser. Excerpta Med., 403, 594 (1977) and Metabolism, 28, 456 (1976)].

The present inventors have conducted extensive investigations on compounds useful for preventing or treating the above-described complications of chronic diabetes by inhibiting the functions of the aldose reductase, and found that the rhodanine derivatives of the present invention are useful as an aldose reductase inhibitor, and thus completed the present invention.

Further, certain kinds of conventional rhodanine derivatives [for example, the compounds described in the hereinafter given Examples 1, 1(2), 1(7), 1(8), 1(11), 1(13), 1(17), 1(25) and 1(27] which have been known for applications as sensitizer, antimicrobial agents, etc. were also found very useful as an aldose reductase inhibitor.

The present invention relates rhodanine derivatives represented

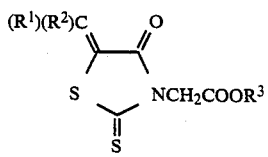

[wherein (I) $R^1$ and $R^2$ are taken together to represent a tetramethylene or pentamethylene group; (II) $R^1$ represents a hydrogen atom, and $R^2$ represents (1) a cycloalkyl or cycloalkenyl group of 4–7 carbon atoms which is unsubstituted or substituted by at least one alkyl group of 1–4 carbon atoms, (2) an anthryl or naphthyl group, (3) a phenyl group which is unsubstituted or substituted by at least one of (a) halogen atom, (b) trifluoromethyl group, (c) hydroxyl group, (d) nitro group, (e) carboxyl group, (f) amino group which may be substituted by alkyl group (s) of 1–4 carbon atoms, (g) alkyl, alkoxy or alkylthio group of 1–5 carbon atoms, (h) phenyl group, (i) heterocyclic group containing at least one of nitrogen, oxygen and sulfur atoms which is unsubstituted or substituted by at least one of the above-described substituents (a) to (h), and (j) alkyl group of 1–4 carbon atoms which is substituted by at least one of the above-described substituents (c), (h) and (i), (4) a heterocyclic group containing at least one of nitrogen, oxygen and sulfur atoms which is unsubstituted or substituted by at least one of oxo group and the above-described substituents (a) to (h) and (j), or (5) a

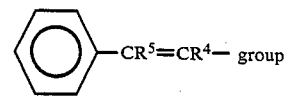

(wherein $R^4$ represents a hydrogen atom, a halogen atom, phenyl group or an alkyl group of 1–5 carbon atoms; and $R^5$ represents a hydrogen atom, a phenyl group or an alkyl group of 1–5 carbon atoms) or

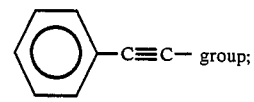

or (III) $R^1$ and $R^2$, which may be the same or different with each other, each represents a phenyl group which is unsubstituted or substituted by at least one of the above-described substituents (a) to (j); and $R^3$ represents a hydrogen atom, an alkyl group of 1–12 carbon atoms, an aralkyl group of 7–13 carbon atoms, a cycloalkyl or cycloalkenyl group of 4–7 carbon atoms which is unsubstituted or substituted by at least one alkyl group of 1–4 carbon atoms, or a phenyl group which is unsubstituted or substituted by at least one of the above-described substituents (a) to (j)] and, when $R^3$ represents a hydrogen atom, non-toxic salts of the acids.

In particular, the novel compounds of the present invention relate to rhodanine derivatives represented by the general formula:

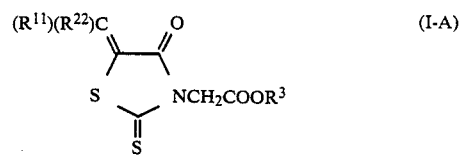

[wherein (I) $R^{11}$ and $R^{22}$ are taken together to represent a tetramethylene or pentamethylene group; (II) $R^{11}$ represents a hydrogen atom, and $R^{22}$ represents (1) a cycloalkyl or cycloalkenyl group of 4–7 carbon atoms which is unsubstituted or substituted by at least one alkyl group of 1–4 carbon atoms, (2) an anthryl or naphthyl group, (3) a phenyl group which is substituted by at least one of (a-1) chlorine or fluorine atom, (b) trifluoromethyl group, (c) hydroxyl group, (f) amino group which may be substituted by alkyl group (s) of 1–4 carbon atoms, (g-1) alkyl or alkylthio group of 1–5 carbon atoms, (g-2) alkoxy group of 2–5 carbon atoms, (h) phenyl group, (i) heterocyclic group containing at least one of nitrogen, oxygen and sulfur atoms which is unsubstituted or substituted by at least one of (a) halogen atom, (d) nitro group, (e) carboxyl group and (g) alkyl, alkoxy or alkylthio group of 1–5 carbon atoms and the above-described substituents (b), (c), (f) and (h), and (j) alkyl group of 1-4 carbon atoms which is substituted by at least one of the above-described substituents (c), (h) and (i), (4)

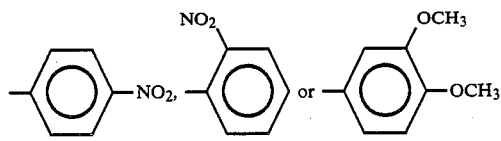

group, (5) a heterocyclic group containing at least one of nitrogen, oxygen and sulfur atoms which is unsubstituted or substituted by at least one of oxo group and the above-described substituents (a-1), (b), (c), (d), (e), (f), (g), (h) and (j) (providing that pyridyl, 3-indolyl, 2-and 4-quinolyl, 2-furyl, 5-nitro-2-furyl and 6-methyl-2-pyridyl groups are excluded), (6) a

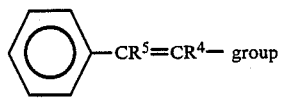

(wherein $R^4$ represents a hydrogen atom, a halogen atom, a phenyl group or an alkyl group of 1-5 carbon atoms; and $R^5$ represents a hydrogen atom, a phenyl group or an alkyl group of 1-5 carbon atoms, but when, one of the $R^4$ and $R^5$ is hydrogen atom, the other is not hydrogen atom) or

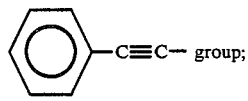

or (III) $R^{11}$ and $R^{22}$, which may be the same or different with each other, each represents a phenyl group which is unsubstituted or substituted by at least one of the above-described substituents (a), (b), (c), (d), (e), (f), (g), (h), (i) and (j); and $R^3$ represents a hydrogen atom, an alkyl group of 1-12 carbon atoms, an aralkyl group of 7-13 carbon atoms, a cycloalkyl or cycloalkenyl group of 4-7 carbon atoms which is unsubstituted or substituted by at least one alkyl group of 1-4 carbon atoms, or a phenyl group which is unsubstituted or substituted by at least one of the above-described substituents (a), (b), (c), (d), (e), (f), (g), (h), (i) and (j)] and, when $R^3$ represents a hydrogen atom, non-toxic salts of the acids.

"Alkyl group" used throughout the specification including claims means a straight chain or branched chain alkyl group.

The cycloalkyl and cycloalkenyl groups of 4-7 carbon atoms which are unsubstituted or substituted by at least one alkyl group of 1-4 carbon atoms represented by $R^2$, $R^3$ or $R^{22}$ include cyclobutyl, 1-propyl-cyclobutyl, 1-butylcyclobutyl, 2-methylcyclobutyl, 2-propylcyclobutyl, 3-ethylcyclobutyl, 3-propylcyclobutyl, 2,3,4-triethylcyclobutyl, cyclopentyl, 3-ethylcyclopentyl, 3-propylcyclopentyl, 3-butylcyclopentyl, 3-tert-butylcyclopentyl, 2,2-dimethylcyclopentyl, (1-methyl-3propyl) cyclopentyl, (2-methyl-3-propyl)cyclopentyl, (2-methyl-4-propyl)cyclopentyl, cyclohexyl, 3-ethylcyclohexyl, 3-isopropylcyclohexyl, 4-methylcyclohexyl, 4-ethylcyclohexyl, 4-propylcyclohexyl, 4-tert-butylcyclohexyl, 2,2-dimethylcyclohexyl, 2,6-dimethylcyclohexyl, (2,6-dimethyl-4-propyl) cyclohexyl, cycloheptyl, 2-cyclohexenyl, 3-cyclohexenyl and 2-cyclopentenyl groups, etc.

The phenyl group which is unsubstituted or substituted by at least one of the above-described substituents (a) to (j), represented by $R^1$, $R^2$, $R^3$, $R^{11}$ and $R^{22}$, includes phenyl, 2-, 3- or 4-bromophenyl, 2-, 3- or 4-iodophenyl, 2-, 3- or 4-chlorophenyl, 2,4dichlorophenyl, 2,4,6-trichlorophenyl, 2,3,4,5,6-pentafluorophenyl, 3-trifluoromethylphenyl, 2-, 3- or 4-hydroxyphenyl, 2-hydroxy-5-chlorophenyl, 2-, 3- or 4-nitrophenyl, 2-, 3- or 4-carboxyphenyl, 2-, 3- or 4-aminophenyl, 4-(N,N-dimethyl)aminophenyl, 4-(N,N-diethyl)aminophenyl, 2-, 3- or 4-tolyl, 2-, 3- or 4-ethylphenyl, 2-, 3- or 4-isopropylphenyl, 2-, 3- or 4-tert-butylphenyl, 4-sec-butylphenyl, 2,4-dimethylphenyl, 2,5-dimethylphenyl, 2,6-dimethylphenyl, 2,6-diethylphenyl, (2-isopropyl-5-methyl)phenyl, 2,6-diisopropylphenyl, (2-tert-butyl-6-methyl)phenyl, (2-tert-butyl -4-methyl)phenyl, 2,4-di-tert-butylphenyl, 2,6-di-tert-butylphenyl, 3,5-di-tert-butylphenyl, 2,4,6-trimethylphenyl, (2-tert-butyl-4,6-dimethyl)phenyl, (2,6-di-tert-butyl-4-methyl)phenyl, 2,4,6-tri-tert-butylphenyl, 2-, 3- or 4-methoxyphenyl, 2-, 3- or 4-ethoxyphenyl, 3,4-dimethoxyphenyl, 3-ethoxy-4-isopentyloxyphenyl, 2-, 3- or 4-methylthiophenyl, 2-, 3- or 4-ethylthiophenyl, 4-biphenyl, 4-(3-pyridyl) phenyl, 4-(4-pyridyl)phenyl, 4-(1-imidazolyl)phenyl, 3-(1-imidazolyl)phenyl, 2-(1-imidazolyl)phenyl, 4-(2-indolyl)phenyl, 4-benzylphenyl, 4-(α-hydroxybenzyl)phenyl, 4-(2-thienylmethyl)phenyl, 4-(2-furylmethyl) phenyl, 4-(3-pyridylmethyl)phenyl, 4-[2-(3-pyridyl)ethyl]phenyl, 4-[(3-pyridyl)-hydroxymethyl]phenyl, 4-[2-(3-pyridyl)ethyl]phenyl, 4-(4-pyridylmethyl)phenyl, 3-(4-pyridylmethyl)phenyl, 3-(3-pyridylmethyl) phenyl, 3-methyl-4-(3-pyridylmethyl)phenyl, 4-(4-methyl-3-pyridylmethyl)phenyl, 4-(4-methyl-3-pyridyl)hydroxymethylphenyl, 2-(1-imidazolylmethyl)phenyl, 3-(1-imidazolylmethyl)phenyl, 4-(1-imidazolylmethyl)phenyl, 4-[2-(1-imidazolyl)-ethyl]phenyl, and 4-[3-(1-imidazolyl)propyl]phenyl groups, etc.

The heterocyclic group containing at least one of nitrogen, oxygen and sulfur atoms which is unsubstituted or substituted by at least one of oxo group and the above-described substituents (a) to (h) and (j), represented by $R^2$ or $R^{22}$, includes 2-pyridyl, 3-pyridyl, 4-pyridyl, 4-methyl-3-pyridyl, 6-methyl-2-pyridyl, 2-thienyl, 2-furyl, 5-nitro-2-furyl, 5hydroxymethyl-2-furyl, 2-pyrrolyl, 3-indolyl, 5-indolyl, 5-bromo-3-indolyl, 5-chloro-3-indolyl, 5-methyoxy-3-indolyl, 2-isopropyl-5-methoxy -3-indolyl, 5-nitro-3-indolyl, 5-carboxy-3-indolyl, 1-methyl-3-indolyl, 1-butyl-3-indolyl, 2-methyl-3-indolyl, 2-isopropyl-3-indolyl, 2-phenyl-3-indolyl, 1-benzyl-3-indolyl, 2-isopropyl-5-nitro-3-indolyl, 2-quinolyl, 3-quinolyl, 4-quinolyl, 3-benzo[b]furyl, 3-benzo[b]thienyl, 4-oxo-2-chromanyl, 5-(3-pyridylmethyl)-2-thienyl, 5-(1-imidazolylmethyl)-2-thienyl, 5-(3-pyridylmethyl)-2-furyl and 5-(1-imidazolylmethyl)-2-furyl groups, etc.

The alkyl group of 1-12 carbon atoms represented by $R^3$ includes methyl, ethyl, propyl, butyl, pentyl, hexyl, heptyl, octyl, nonyl, decyl, undecyl and dodecyl groups and isomers thereof, and the aralkyl group of 7-13 carbon atoms represented by $R^3$ includes benzyl, 1-phenylethyl, 2-phenylethyl, 3-phenylbutyl, 4-phenylbutyl, 1-(2-naphthyl)-ethyl, 2-(1-naphthyl)ethyl, and biphenylmethyl groups.

The alkyl group of 1-5 carbon atoms represented by $R^4$ or $R^5$ includes methyl, ethyl, propyl, butyl and pentyl groups and isomers thereof.

Preferable heterocyclic groups represented by $R^2$ or $R^{22}$ are monocyclic or bicyclic heterocyclic groups containing one or more of nitrogen, oxygen and sulfur atoms, and aromatic heterocyclic groups are more preferable. They may be unsubstituted or suitably substituted with the above-described substituents.

Preferable $R^2$ and $R^{22}$ are cyclohexyl, 3-cyclohexenyl, 9-anthryl, 1-naphthyl, 2-naphthyl, phenyl, 4-chlorophenyl, 3-chlorophenyl, 2-chlorophenyl, 2,4-dichlorophenyl, 2-iodophenyl, 3-iodophenyl, 4-iodophenyl, 2,3,4,5,6-pentafluorophenyl, 4-hydroxyphenyl, 2-hydroxy-5-chlorophenyl, 2-nitrophenyl, 3-nitrophenyl, 4-nitrophenyl, 2-carboxyphenyl, 4-carboxyphenyl, 4-(N,N-dimethylamino)phenyl, 4-tolyl, 4-methoxyphenyl, 3,4-dimethoxyphenyl, 4-biphenyl, 4-(3-pyridylmethyl)phenyl, 4-(α-hydroxybenzyl)-phenyl, 3-pyridyl, 4-pyridyl, 2-thienyl, 2-furyl, 5-nitro-2-furyl, 5-hydroxymethyl-2-furyl, 2-pyrrolyl, 3-indolyl, 5-indolyl, 5-bromo-3-indolyl, 5-chloro-3-indolyl, 5-methoxy-3-indolyl, 2-isopropyl-5-methoxy-3-indolyl, 5-nitro-3-indolyl, 5-carboxy-3-indolyl, 1-methyl-3-indolyl 2-methyl-3-indolyl, 2-isopropyl-3-indolyl, 2-phenyl-3-indolyl, 3-quinolyl, 3-benzo[b]furyl, 3-benzo[b]thienyl, 4-oxo-2-chromanyl, 5-(3-pyridylmethyl)-2-thienyl, 4-[(3-pyridyl)hydroxymethyl]phenyl, 3-ethoxy-4-isopentyloxyphenyl, 1-benzyl-3-indolyl, 1-butyl-3-indolyl, 2-isopropyl-5-nitro-3-indolyl, styryl, α-methylstyryl, α-ethylstyryl, α-isopropylstyryl, α-pentylstyryl, α-phenylstyryl, α-bromostyryl, α-chlorostyryl, β-methylstyryl, β-propylstyryl, β-phenylstyryl, α, β-dimethylstyryl, and 2-phenylethynyl groups.

Preferable $R^3$ is a hydrogen atom or an alkyl group of 1-12 carbon atoms, more preferably a hydrogen atom or an alkyl group of 1-4 carbon atoms, and most preferably a hydrogen atom.

According to the present invention, the rhodanine derivative represented by the general formula (I) may be obtained by reacting a compound represented by the general formula:

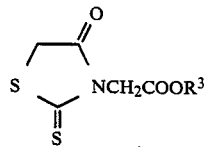

(II)

(wherein $R^3$ represents the same meaning as described above) with a compound represented by the general formula:

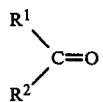

(III)

(wherein $R^1$ and $R^2$ represent the same meanings as described above).

The reaction may be carried out in acetic acid in the presence of sodium acetate at from room temperature to a refluxing temperature of a reaction solvent. The reaction product may be purified by a usual purification methods, such as recrystallization, thin layer, column or high speed liquid chromatography using silica gel, etc.

The starting materials represented by the general formula (II) or (III) are known per se or may be prepared by known processes.

The esters represented by the general formula (I) wherein, $R^3$ represents the group other than a hydrogen atom with the other symbols representing the same meanings as described above, may be prepared by esterification of the corresponding carboxylic acids represented by the general formula (I) wherein, $R^3$ represents a hydrogen atom with the other symbols representing the same meanings as described above, by methods known per se. Methods for the esterification of carboxylic acids are well known. For example, the esterification can be conducted by (1) a process of using a diazoalkane, or (2) a process of using an N,N-dimethylformamide-dialkylacetal [cf. Helv. Chim. Acta., 48, 1746 (1965)] in cases where $R^3$ represents an alkyl group, or (3) a process of using an alkyl halide or an aralkyl halide in cases where $R^3$ represents an alkyl group or an aralkyl group, or (4) a process of using dicyclohexylcarbodiimide [cf. the specification of Japanese Pat. No. 762305], (5) a process of using a pivaloyl halide [cf. the specification of Japanese Pat. No. 756972], (6) a process of using an alkylsulfonyl halide or an arylsulfonyl halide [cf. the specification of Japanese Pat. No. 759351], (7) a process of using isobutyl chloroformate [cf. the specification of British Pat. No. 1492439], (8) a process of using dipyridyl disulfide and triphenylphosphine [cf. Tetrahedron Letters, 3409 (1976)], or a process as disclosed in "Compendium of Organic Synthetic Methods", Section 107 of Vol. 1 (1971), Vol. 2 (1974) and Vol. 3 (1977) published by John Wiley & Sons, Inc. (U.S.A.) in cases where $R^3$ represents an alkyl group or an aralkyl group or an another esterifiable functional group within the definition of $R^3$.

The compounds represented by the general formula (I) wherein $R^3$ represents a hydrogen atom may be converted into their salts by known methods. Preferably, the salts are non-toxic salts. The term "non-toxic salts" used in this specification mean salts of cations of which are relatively innocuous to the animal organism, when used in an amount required for the treatment, so that the beneficial pharmacological properties of the compounds represented by the general formula (I) are not vitiated by the side-effects ascribable to those cations. The salts are preferably water-soluble. Suitable salts include salts of alkali metals such as sodium or potassium, salts of alkaline earth metals such as calcium or magnesium, ammonium salts and pharmaceutically acceptable (i.e., non-toxic) amine salts. Suitable amines which form such salts with carboxylic acids are well known and include, for example, amines derived in theory by the replacement of one or more of the hydrogen atoms of ammonia by other groups. Such groups, which may be the same or different with each other when more than one hydrogen atom is replaced, are selected from, for example, alkyl groups of 1-6 carbon atoms and hydroxyalkyl groups of 2 or 3 carbon atoms. As a preferred non-toxic amine salt, there are illustrated a tetraalkylammonium salts such as tetramethylammonium salts and organic amine salts such as methylamine salts, ethylamine salts, isopropylamine salts, a tert-butylamine salts, dimethylamine salts, cyclopentylamine salts, benzylamine salts, phenetylamine salts, piperidine salts, monoethanolamine salts, diethanolamine salts, lysine salts, arginine salts and N-methyl-D-glucamine salts.

The salts may be preferred from the acids represented by the general formula (I) wherein $R^3$ represents a hydrogen atom according to known methods, for example, by reaction of stoichiometric quantities of an acid represented by the general formula (I) and an appropriate base, such as a hydroxide or carbonate of an alkali metal, alkaline earth metal, ammonium hydroxide, ammonia or an organic amine in a suitable solvent. The salts may be isolated by lyophilisation of the solution, or, if it is sufficiently insoluble in the reaction solvent, by filtration, if necessary after removal of part of the solvent.

Since the rhodanine derivatives represented by the general formula (I) according to the present invention process an activity of inhibiting an aldose reductase which reduces an aldose to the corresponding polyol, they are useful as an aldose reductase inhibitor. This means that they are useful for the prevention and treatment of nerve disturbances such as neuralgia, retinopathy, diabetic cataract and renal disturbances such as tubular nephropathy which are known as complications due to an aldose reductase among the complications of chronic diabetes such as circulatory disturbances, renal disturbances, retinopathy, diabetic cataract, nerve disturbances, infections, etc. [cf. Jap. J. Ophthalmol., 20, 399 (1976), Int. Congr. Ser. Excerpta Med., 403, 594 (1977) and Metabolism, 28, 456 (1979)].

For example, according to experiments in a laboratory conducted in accordance with the method as described in J. Biol. Chem., 240, 877 (1965) using an aldose reductase obtained from the crystalline lenses of rats, the rhodanine derivatives represented by the general formula (I) produced a 50% inhibition of the aldose reductase at $10^{-7}$–$10^{-9}$ molar concentrations.

Further, the effect of inhibiting sorbitol accumulation in cultivated crystalline lenses of rats were examined according to the methods as described in J. Biol. Chem., 240, 310 (1965) and "Methods of Enzymatic Analysis" pp. 1323 (1963) published by Academic Press. Ind. (N.Y. and London), and the rhodanine derivatives represented by the general formula (I) produced a 50% inhibition of the sorbitol accumulation at $10^{-5}$–$10^{-6}$ molar concentrations.

Furthermore, motor nerve conduction velocity was determined used streptozotocin-induced diabetic Wister strain rats according to the method of Miyoshi [the method disclosed in "Fukuoka Ishi", 62 (7), 588–603 (1971)] and, as a result, the rhodanine derivatives represented by the general formula (I) showed significant effects. For example, when 3-carboxymethyl-5-benzylidenerhodanine was orally administered to the diabetic rats at a dose of 100 mg/Kg-animal body weight in a single dosage per day for 2 weeks and the motor nerve conduction velocity was then determined, no change was observed in the blood sugar level and revealed that the motor nerve conduction velocity was almost the same as that of normal rats. This fact does not indicate that the rhodanine derivatives are useful for treating diabetes per se, but does indicate that they can be used for treating nerve disturbance which is one of the complication of diabetes.

On the other hand, when the rhodanine derivatives represented by the general formula (I) was orally administered to mice at a dose of 1 g/Kg-animal body weight to determine acute toxicity, there was no death case and any abnormality was not recognized in various organs. In addition, experiments on cytotoxicity were conducted using Raji Cells, and the 50% growth inhibition concentrations ($TCID_{50}$) of the rhodanine derivatives included in the present invention were $10^{-4}$–$10^{-5}$ molar concentrations.

The present invention further includes in its scope pharmaceutical compositions containing at least one of the rhodanine derivatives represented by the general formula (I) or non-toxic salts thereof as an active ingredient, together with a pharmaceutically inert carriers or coating. These pharmaceutical composition may be prepared by conventional processes well-known to the art. Examples of such compositions include tablets, pills, powders, granules, capsules, suppositories, injections, eye drops and the like. These pharmaceutical compositions are clinically administered orally, intrarectally, parenterally (e.g., intravenously, intramuscularly, subcutaneously or intraperitoneally), or as eye drops, preferably orally. Doses for the prevention or treatment of the abovedescribed complications of diabetes due to an aldose reductase are determined depending upon the desired therapeutic effect, the route of administration, the duration of the treatment, age, body weight and the like. The dose per day for a patient is generally, for example, about 0.1–100 mg/Kg-body weight, preferably about 0.25–5.0 mg/Kg-body weight, for oral administration.

Preferred novel rhodanine derivatives included in the present invention include 3-carboxymethyl-5-diphenylmethylenerhodanine, 3-carboxymethyl-5-cyclopentylidenerhodanine, 3-carboxymethyl-5-cyclohexylidenerhodanine, 3-carboxymethyl-5-cyclohexylmethylenerhodanine, 3-carboxymethyl-5-(3-cyclohexenylmethylene)rhodanine, 3-carboxymethyl-5-(9-anthrylmethylene)rhodanine, 3-carboxymethyl-5-(1-naphthylmethylene)rhodanine, 3-carboxymethyl-5-(2-naphthylmethylene)rhodanine, 3-carboxymethyl-5-(4-chlorobenzylidene)rhodanine, 3-carboxymethyl-5-(3-chlorobenzylidene)-rhodanine, 3-carboxymethyl-5-(2-chlorobenzylidene)rhodanine, 3-carboxymethyl-5-(2,4-dichlorobenzylidene)rhodanine, 3-carboxymethyl-5-(2,3,4,5,6-pentafluorobenzylidene)rhodanine, 3-carboxymethyl-5-(4-hydroxybenzylidene)rhodanine, 3-carboxymethyl-5-(2-hydroxy-5-chlorobenzylidene)rhodanine, 3-carboxymethyl-5-(2-nitrobenzylidene)rhodanine, 3-carboxymethyl-5-(4-nitrobenzylidene)rhodanine, 3-carboxymethyl-5-[4-(N,N-dimethylamino)benzylidene]rhodanine, 3-carboxymethyl-5-(4-methylbenzylidene)rhodanine, 3-carboxymethyl-5-(3,4-dimethoxybenzylidene)rhodanine, 3-carboxymethyl-5-(4-phenylbenzylidene)rhodanine, 3-carboxymethyl-5-[4-(3-pyridylmethyl)benzylidene]rhodanine, 3-carboxymethyl-5-[4-(α-hydroxybenzyl)benzylidene]rhodanine, 3-carboxymethyl-5-(2-thienylmethylene)rhodanine, 3-carboxymethyl-5-(5-hydroxymethyl-2-furylmethylene)rhodanine, 3-carboxymethyl-5-(2-pyrrolylmethylene)rhodanine, 3-carboxymethyl-5-(5-chloro-3-indolylmethylene)rhodanine, 3-carboxymethyl-5-(5-methoxy-3-indolylmethylene)rhodanine, 3-carboxymethyl-5-(2-isopropyl-5-methoxy-3-indolylmethylene)rhodanine, 3-carboxymethyl-5-(5-nitro-3-indolylmethylene)rhodanine, 3-carboxymethyl-5-(5-carboxy-3-indolylmethylene)rhodanine, 3-carboxymethyl-5-(1-methyl-3-indolylmethylene)rhodanine, 3-carboxymethyl-5-(2-methyl-3-indolylmethylene)rhodanine, 3-carboxymethyl-5-(2-phenyl-3-indolylmethylene)rhodanine, 3-carboxymethyl-5-(5-indolylmethylene)rhodanine, 3-carboxymethyl-5-(3-quinolylmethylene)rhodanine, 3-carboxymethyl-5-(3-benzo[b]-furylmethylene)rhodanine, 3-carboxymethyl-5-(3-benzo[b]thienylmethylene)rhodanine, 3-carboxymethyl-5-(4-oxo-2-chromanylmethylene)rhodanine, 3-carboxymethyl-5-[5-(3-pyridylmethyl)-2-thienylmethylene]rhodanine, 3-carboxymethyl-5-(2-methylcinnamylidene)rhodanine, 3-carboxymethyl-5-(2-phenylethynylmethylene)rhodanine, 3-carboxymethyl-5-{4-[(3-pyridyl)hydroxymethyl]benzylidene}rhodanine, 3-carboxymethyl-5-(3-ethoxy-4-isopentyloxybenzylidene)rhodanine, 3-carboxymethyl-5-(1-benzyl-3-indolylmethylene)rhodanine, 3-carboxymethyl-5-(1-butyl-3-indolylmethylene)rhodanine, 3-carboxymethyl-5-(2-isopropyl-5-nitro-3-indolylmethylene)rhodanine, 3-carboxymethyl-5-(2-ethylcinnamylidene)rhodanine, 3-carboxymethyl-5-(2-isopropylcinnamylidene)rhodanine, 3-carboxymethyl-5-(2-pentylcinnamylidene)rhodanine, 3-carboxymethyl-5-(2-phenylcinnamylidene)rhodanine, 3-carboxymethyl-5-(2-bromocinnamylidene)rhodanine, 3-carboxymethyl-5-(2-chlorocinnamylidene)rhodanine, 3-carboxymethyl-5-(3-methylcinnamylidene)rhodanine, 3-carboxymethyl-5-(3-propylcinnamylidene)rhodanine, 3-carboxymethyl-5-(3-phenylcinnamylidene)rhodanine, and 3-carboxymethyl-5-(2,3-dimethylcinnamylidene)rhodanine, and esters and non-toxic salts thereof. Further, the known rhodanine derivatives include 3-carboxymethyl-5-benzylidenerhodanine, 3-carboxymethyl-5-(2-iodobenzylidene)rhodanine, 3-carboxymethyl-5-(3-iodobenzylidene)rhodanine, 3-carboxymethyl-5-(4-iodobenzylidene)rhodanine, 3-carboxymethyl-5-(3-nitrobenzylidene)rhodanine, 3-carboxymethyl-5-(2-carboxybenzylidene)rhodanine, 3-carboxymethyl-5-(4-carboxybenzylidene)rhodanine, 3-carboxymethyl-5-(4-methoxybenzylidene)rhodanine, 3-carboxymethyl-5-(3-pyridylmethylene)rhodanine, 3-carboxymethyl-5-(4-pyridylmethylene)rhodanine, 3-carboxymethyl-5-(3-indolylmethylene)rhodanine, 3-carboxymethyl-5-(5-bromo-3-indolylmethylene)rhodanine, 3-carboxymethyl-5-(2-furylmethylene)rhodanine, 3-carboxymethyl-5-(5-nitro-2-furylmethylene)rhodanine, and 3-carboxymethyl-5-styrylmethylenerhodanine, and the esters and non-toxic salts thereof.

The following Examples each illustrates an example of the present invention. "TLC", "NMR" and "MS" in the Examples represent "thin layer chromatography", "nuclear magnetic resonance spectrum" and "mass spectrum", respectively. The solvents in the parentheses of TLC indicate the developing solvents used, and the proportion thereof means a volume ratio. The parentheses following the melting points indicate the solvents for recrystallization. "NMR" are recorded in dimethyl sulfoxide-$d_6$ solution unless specifically described.

Example 1

3-Carboxymethyl-5-Benzylidenerhodanine

A mixture of 955 mg of 3-carboxymethylrhodanine, 516 mg of sodium acetate, 10 ml of acetic acid and 637 mg of benzaldehyde was heat-refluxed for 2 hours. To the reaction mixture was added 20 ml of water, and the precipitated crystals were filtered. The resulting crystals were recrystallized from ethanol to obtain 699 mg of the titled compound.
Melting Point: 254°–256° C.
NMR: $\delta = 7.88$ (1H, s), 7.59 (5H, m), 4.76 (2H, s).
MS: m/e=279, 134, 91.

In the same manner, the following compounds were obtained from the corresponding aldehydes or ketones.

(1) 3-Carboxymethyl-5-(4-chlorobenzylidene)rhodanine
Yield: 57%.
Melting Point: 272°–274° C. (ethanol-acetic acid).
NMR: $\delta = 7.88$ (1H, s), 7.65 (4H, s), 4.76 (2H, s).
MS: m/e=315, 313, 170, 168, 133, 89.

(2) 3-Carboxymethyl-5-(4-methoxybenzylidene)rhodanine
Yield: 52%.
Melting Point: 250°–253° C. (water-ethanol).
NMR: $\delta = 7.84$ (1H, s), 7.64 (2H, d), 7.12 (2H, d), 4.75 (2H, s), 3.86 (3H, s).
MS: m/e=309, 164, 149, 121.

(3) 3-Carboxymethyl-5-(3-chlorobenzylidene)rhodanine
Yield: 54%.
Melting Point: 227°–229° C. (ethanol).
NMR: $\delta = 7.88$ (1H, s), 7.74 (1H, wide s), 7.59 (3H, m), 4.76 (1H, s).
MS: m/e=315, 313, 170, 168, 133, 89.

(4) 3-Carboxymethyl-5-(2-chlorobenzylidene)rhodanine
Yield: 65%.
Melting Point: 238°–242° C. (water-ethanol).
NMR: $\delta = 7.98$ (1H, s), 7.58 (4H, m), 4.77 (2H, s).
MS: m/e=315, 313, 278, 170, 168, 133, 125, 89.

(5) 3-Carboxymethyl-5-(4-nitrobenzylidene)rhodanine
Yield: 74%.
Melting Point: 274°–277° C. (ethanol-acetic acid).
NMR: $\delta = 8.34$ (2H, d), 7.94 (1H, s), 7.88 (2H, d), 4.78 (2H, s).
MS: m/e=324, 209, 179, 149, 133, 121, 89.

(6) 3-Carboxymethyl-5-(4-hydroxybenzylidene)rhodanine
Yield: 37%.
Melting Point: more than 300° C. (water-ethanol)
NMR: $\delta = 7.66$ (1H, s), 7.47 (2H, d), 6.95 (2H, d), 4.44 (2H, s).
MS: m/e=295, 278, 150.

(7) 3-Carboxymethyl-5-(3-pyridylmethylene)rhodanine
Yield: 64%.
Melting Point: 261°–264° C. (ethanol-acetic acid).
NMR: $\delta = 8.91$ (1H, d), 8.70 (1H, dd), 8.03 (1H, dt), 7.95 (1H, s), 7.61 (1H, dd), 4.88 (2H, s).
MS: m/e=280, 238, 209, 163, 135, 108, 91.

(8) 3-Carboxymethyl-5-(4-pyridylmethylene)rhodanine
Yield: 25%.
Melting Point: 263°–266° C., decomposition (ethanol-acetic acid).
NMR: $\delta = 8.85$ (2H, m), 7.87 (1H, s), 7.60 (2H, m), 4.77 (2H, s).
MS: m/e=280, 163, 135, 108, 91, 72.

(9) 3-Carboxymethyl-5-(2-thienylmethylene)rhodanine
Yield: 50%.
Melting Point: more than 209° C. (water-ethanol)
NMR: $\delta = 8.17$ (1H, s), 8.12 (1H, dd), 7.80 (1H, dd), 7.34 (1H, dd), 4.74 (2H, s).
MS: m/e=285, 149, 140.

(10) 3-Carboxymethyl-5-(2,4-dichlorobenzylidene)rhodanine
Yield: 73%.

Melting Point: 237° C. or more (ethanol-water-acetic acid).
NMR: δ=7.89 (1H, s), 7.84 (1H, dd), 7.62 (2H, m), 4.76 (2H, s).
MS: m/e=347, 312, 204, 202, 167, 149, 123.

(11) 3-Carboxymethyl-5-(3-indolylmethylene)rhodanine
Yield: 28%.
Melting Point: more than 300° C. (water-ethanol)
NMR: δ=12.44 (1H, wide s), 8.13 (1H, s), 7.95 (1H, m), 7.92 (1H, s), 7.55 (1H, m), 7.28 (2H, m), 4.69 (2H, s).
MS: m/e=318, 223, 173, 129.

(12) 3-Carboxymethyl-5-diphenylmethylenerhodanine
Yield: 3.3%.
TLC (ethanol:ethyl acetate=1:9): Rf=0.25.
NMR (methanol-d$_4$ solution): δ=7.35 (10H, m), 4.67 (2H, s).
MS: m/e=355, 210, 178, 165.

(13) 3-Carboxymethyl-5-(4carboxybenzylidene)rhodanine
Yield: 40.9%.
Melting Point: 300° C. or more (acetic acid-ethanol-water).
NMR: δ=8.16-7.98 (2H, d), 7.86 (1H, s), 7.81-7.59 (2H, d), 4.64 (2H, s).
MS: m/e=323, 179, 178, 161, 89, 72.

(14) 3-Carboxymethyl-5-[4-(N,N-dimethylamino)-benzylidene]rhodanine
Yield: 10.6%.
Melting Point: 260°-264° C. (acetic acid-ethanol).
NMR (acetone-d$_6$+dimethyl-sulfoxide-d$_6$ solution): δ=7.72 (1H, s), 7.60-7.40 (2H, d), 7.00-6.78 (2H, d), 4.78 (2H, s), 3.11 (6H, s).
MS: m/e=322, 177, 176.

(15) 3-Carboxymethyl-5-(2,3,4,5,6-pentafluorobenzylidene)rhodanine
Yield: 68.9%.
Melting Point: 177°-184° C. (cyclohexane-ethanol).
NMR (acetone-d$_6$ solution): δ=7.69 (1H, s), 4.87 (2H, s).
MS: m/e=370, 369, 226, 225, 224, 192, 180, 161, 72.

(16) 3-Carboxymethyl-5-(4-methylbenzylidene)rhodanine
Yield: 49.5%.
Melting Point: 245°-250° C. (acetic acid).
NMR (acetone-d$_6$+dimethyl sulfoxide-d$_6$ solution): δ=7.81 (1H, s), 7.66-7.49 (2H, d), 7.49-7.32 (2H, d), 4.80 (2H, s), 2.41 (3H, s).
MS: m/e=294, 293, 149, 148, 147, 115, 91.

(17) 3-Carboxymethyl-5-(2-carboxybenzylidene)rhodanine
Yield: 12%.
Melting Point: more than 300° C. (water-ethanol)
NMR: δ=8.62 (1H, s), 7.92 (1H, m), 7.55 (3H, m), 4.58 (2H, s).
MS: m/e=323, 178, 173, 160, 150, 133, 105, 77.

(18) 3-Carboxymethyl-5-(9-anthrylmethylene)rhodanine
Yield: 36.3%.
Melting Point: 277°-279° C. (acetic acid).
NMR: δ=8.80 (2H, s), 8.30-7.46 (8H, m), 4.82 (2H, s).
MS: m/e=379, 234, 229, 202, 117.

(19) 3-Carboxymethyl-5-(5-methoxy-3-indolylmethylene)rhodanine
Yield: 70%.
Melting Point: 266° C., decomposition (acetic acid).
NMR: δ=12.27 (1H, m), 8.17 (1H, s), 7.84 (1H, d), 7.51 (1H, d), 7.40 (1H, d), 6.88 (1H, dd), 4.72 (2H, s), 3.84 (3H, s).
MS: m/e=348, 204, 203, 188, 160.

(20) 3-Carboxymethyl-5-(4-phenylbenzylidene)rhodanine
Yield: 53%.
Melting Point: 258°-262° C. (water-acetic acid).
NMR: δ=7.91 (1H, s), 7.9-7.4 (9H, m), 4.76 (2H, s).
MS: m/e=355, 211, 210, 165, 105.

(21) 3-Carboxymethyl-5-(1-naphthylmethylene)rhodanine
Yield: 74%.
Melting Point: 241°-244° C. (water-acetic acid).
NMR: δ=8.51 (1H, s), 8.3-7.9 (3H, m), 7.8-7.5 (4H, m), 4.79 (2H, s).
MS: m/e=329, 185, 184, 152, 139.

(22) 3-Carboxymethyl-5-(2-naphthylmethylene)rhodanine
Yield: 63%.
Melting Point: 257°-264° C. (water-acetic acid).
NMR: δ=8.21 (1H, wide s), 8.15-7.8 (4H, m), 7.8-7.5 (3H, m), 4.76 (2H, s).
MS: m/e=329, 185, 184, 152, 141, 139.

(23) 3-Carboxymethyl-5-(2-hydroxy-5-chlorobenzylidene)rhodanine
Yield: 34.2%.
Melting Point: 243°-247° C. (acetic acid-water-ethanol).
NMR: δ=7.90 (1H, s), 7.49-7.30 (1H, m), 7.36 (1H, s), 7.08-6.92 (1H, m), 4.74 (2H, s).
MS: m/e=329, 214, 212, 186, 184, 155, 149, 121, 117, 95, 89, 72, 55.

(24) 3-Carboxymethyl-5-{4-[(3-pyridyl)hydroxymethyl]benzylidene}rhodanine
Yield: 86%.
Melting Point: 287°-290° C. (recrystallization was not done).
NMR: δ=8.70-8.35 (2H, m), 7.85 (1H, s), 7.84-7.70 (1H, m), 7.62 (4H, s), 7.45-7.25 (1H, m), 5.88 (1H, s), 4.74 (2H, s).
MS: m/e=386, 342, 242, 241, 239, 225, 163, 161, 149, 135, 44.

(25) 3-Carboxymethyl-5-cinnamylidenerhodanine
Yield: 31.2%.
Melting Point: more than 217° C. (water-ethanol).
NMR: δ=7.83-6.93 (8H, m), 4.71 (2H, s).
MS: m/e=305, 160, 127, 115.

(26) 3-Carboxymethyl-5-cyclohexylidenerhodanine
Yield: 16.7%.
Melting Point: 196°-201° C. (acetic acid).
NMR (CDCl$_3$ solution): δ=9.35 (1H, m), 4.85 (2H, s), 3.13 (2H, m), 2.48 (2H, m), 1.72 (6H, m).
MS: m/e=271, 225, 149, 126, 125, 98, 97.

(27) 3-Carboxymethyl-5-(5-nitro-2-furylmethylene)rhodanine
Yield: 32%.
Melting Point: 238°-242° C. (acetic acid-cyclohexane).
NMR: δ=7.93-7.72 (1H, d), 7.82 (1H, s), 7.50-7.36 (1H, d), 4.74 (2H, s).
MS: m/e=314, 169, 95.

(28) 3-Carboxymethyl-5-(2-phenyl-3-indolylmethylene)rhodanine
Yield: 72%.
Melting Point: 258°-262° C. (acetic acid-water).
NMR: δ=8.03 (1H, s), 7.9 (1H, m), 7.62 (5H, s), 7.7-7.5 (1H, m), 7.4-7.2 (2H, m), 4.72 (2H, s).
MS: m/e=394, 250, 249, 248, 244, 217, 216, 204.

(29) 3-Carboxymethyl-5-(2-methyl-3-indolylmethylene)rhodanine

Yield: 59%.

Melting Point: 291°–292° C. (acetic acid).

NMR: δ=8.02 (1H, s), 7.87 (1H, dd), 7.44 (1H, m), 7.22 (2H, m), 4.73 (2H, s), 2.58 (3H, s).

MS: m/e=332, 187, 186, 154, 144, 115, 77.

(30) 3-Carboxymethyl-5-(2-isopropyl-3-indolylmethylene)rhodanine

Yield: 65%.

Melting Point: 259°–260° C. (acetic acid-water).

NMR: δ=8.11 (1H, s), 7.86 (1H, m), 7.48 (1H, m), 7.24 (2H, m), 4.74 (2H, s), 3.50 (1H, m), 1.37 (6H, d).

MS: m/e=360, 215, 201, 200, 167, 154, 72.

(31) 3-Carboxymethyl-5-(1-methyl-3-indolylmethylene)rhodanine

Yield: 55%.

Melting Point: 282°–288° C. (acetic acid-water).

NMR: δ=8.06 (1H, s), 7.94 (2H, m), 7.57 (1H, m), 7.32 (2H, m), 4.68 (2H, s), 3.93 (3H, s).

MS: m/e=332, 188, 187, 172, 144.

(32) 3-Carboxymethyl-5-(5-chloro-3-indolylmethylene)rhodanine

Yield: 58%.

Melting Point: 278°–282° C. (acetic acid-water).

NMR: δ=8.15 (1H, s), 8.10 (1H, d), 7.96 (1H, d), 7.54 (1H, d), 7.26 (1H, dd), 4.72 (2H, s), 1.92 (1H, s).

MS: m/e=354, 352, 209, 207, 206, 172, 163.

(33) 3-Carboxymethyl-5-(5-nitro-3-indolylmethylene)rhodanine

Yield: 66%.

Mleting Point: more than 300° C. (acetic acid).

NMR: δ=8.96 (1H, d), 8.21 (2H, s), 8.11 (1H, dd), 7.64 (1H, d), 4.73 (2H, s).

MS: m/e=363, 218, 172, 145, 128, 72.

(34) 3-Carboxymethyl-5-[5-(3-pyridylmethyl)-2-thienylmethylene]rhodanine

Yield: 72%.

Melting Point: 254°–256° C. (acetic acid-water).

NMR: δ=8.59 (1H, d), 8.49 (1H, dd), 8.07 (1H, s), 7.75 (1H, dt), 7.66 (1H, d), 7.37 (1H, dd), 7.16 (1H, d), 4.72 (2H, s), 4.32 (2H, s).

MS: m/e=376, 332, 232, 198, 174, 153, 72.

(35) 3-Carboxymethyl-5-(2-methylcinnamylidene)rhodanine

Yield: 64%.

Melting Point: 210°–217° C. (ethanol-water).

NMR: 7.71–7.00 (7H, m), 4.72 (2H, s), 2.21 (3H, s).

MS: m/e=319, 174, 173, 169, 142, 141, 115.

(36) 3-Carboxymethyl-5-(2-pyrrolylmethylene)rhodanine

Yield: 49%.

NMR: δ=7.73 (1H, s), 7.34 (1H, wide s), 6.64 (1H, wide s), 6.45 (1H, wide s), 4.70 (2H, s).

MS: m/e=268, 123, 96, 79.

(37) 3-Carboxymethyl-5-(5-hydroxymethyl-2-furylmethylene)rhodanine

Yield: 14%.

Melting Point: 206°–209° C. (ethanol).

NMR: δ=7.68 (1H, s), 7.21 (1H, d), 6.62 (1H, d), 4.71 (2H, s), 4.54 (2H, s).

MS: m/e=299, 154, 137.

(38) 3-Carboxymethyl-5-(3-cyclohexenylmethylene)rhodanine

Yield: 39%.

Melting Point: 191°–193° C. (ethanol-water).

NMR (CDCl$_3$+dimethyl sulfoxide-d$_6$ solution): δ=6.83 (1H, d), 6.33 (1H, wide s), 5.60 (2H, s), 4.66 (2H, s), 2.40–1.50 (7H, m).

MS: m/e=283, 229, 204, 158, 112, 84, 80.

(39) 3-Carboxymethyl-5-cyclohexylmethylenerhodanine

Yield: 44%.

Melting Point: 214°–217° C. (ethanol-water).

NMR (CDCl$^3$+dimethyl sulfoxide-d$_6$solution): δ=6.80 (1H, d), 6.48 (1H, wide s), 4.66 (2H, s), 2.35–1.00 (11H, m).

MS: m/e=285, 239, 204, 186, 158, 139, 97.

(40) 3-Carboxymethyl-5-(2-isopropyl-5-methoxy-3-indolylmethylene)rhodanine

Yield: 53%.

Melting Point: 255°–260° C. (acetic acid-water).

NMR: δ=12.03 (1H, m), 8.09 (1H, s), 7.38 (1H, d), 7.33 (1H, d), 6.89 (1H, dd), 4.73 (2H, s), 3.82 (3H, s), (1H, m), 1.35 (6H, d).

MS: m/e=390, 346, 286, 230, 202, 200, 187, 110, 91.

(41) 3-Carboxymethyl-5-(1-butyl-3-indolylmethylene)rhodanine

Yield: 35%.

Melting Point: 280°–285° C. (acetic acid).

NMR: δ=8.10 (1H, s), 7.99 (1H, s), 8.06–7.85 (1H, m), 7.75–7.50 (1H, m), 7.50–7.16 (2H, m), 4.72 (2H, s), 4.34 (2H, t), 1.99–1.50 (2H, m), 1.50–1.08 (2H, m), 1.08–0.79 (3H, m).

MS: m/e=374, 229, 189, 96.

(42) 3-Carboxymethyl-5-(1-benzyl-3-indolylmethylene)rhodanine

Yield: 46%.

Melting Point: 269°–273° C. (acetic acid).

NMR: δ=8.18 (1H, s), 8.11 (1H, s), 8.10–7.78 (1H, m), 7.78–7.02 (8H, m), 5.61 (2H, s), 4.71 (2H, s).

MS: m/e=408, 253, 220, 172, 149, 91, 57, 55.

(43) 3-Carboxymethyl-5-(2-isopropyl-5-nitro-3-indolylmethylene)rhodanine

Yield: 81%.

NMR: δ=8.70 (1H, d), 8.11 (1H, dd), 8.08 (1H, s), 7.64 (1H, d), 4.73 (2H, s), 3.51 (1H, m), 1.39 (6H, d).

MS: m/e=405, 271, 260, 245, 199, 149.

(44) 3-Carboxymethyl-5-(2-ethylcinnamylidene)rhodanine

Yield: 58%.

Melting Point: 161°–183° C. (ethanol-water).

NMR: δ=13.4 (1H, m), 7.7–7.1 (7H, m), 4.7 (2H, d), 2.5 (2H, m), 1.18 (3H, m).

MS: m/e=333, 216, 188, 173, 155.

(45) 3-Carboxymethyl-5-(2-isopropylcinnamylidene)rhodanine

Yield: 43%.

TLC (chloroform:methanol=5:1): Rf=0.18.

NMR: δ=7.7–7.2 (6H, m), 7.06 & 6.78 (1H, each s), 4.66 & 4.62 (2H, each s), 3.2 & 2.8 (1H, each m), 1.18 & 1.12 (6H, each d).

MS: m/e=347, 304, 258, 230, 215, 202, 197, 187, 160, 154, 128, 115.

(46) 3-Carboxymethyl-5-(3-ethoxy-4-isopentyloxybenzylidene)rhodanine

Yield: 58%.

Melting Point: 197°–198° C. (ethanol).

NMR: δ=7.80 (1H, s), 7.20 (3H, s), 4.75 (2H, s), 4.30–3.95 (4H, m), 1.90–1.50 (3H, m), 1.38 (3H, t), 0.98 (6H, d).

MS: m/e=409, 339, 194, 165.

(47) 3-Carboxymethyl-5-(2-pentylcinnamylidene)rhodanine

Yield: 40%.
Melting Point: 203°–207° C. (ethanol).
NMR (dimethyl sulfoxide-$d_6$+methanol-$d_6$ solution): $\delta$=7.7–7.0 (7H, m), 4.57 (2H, d), 2.48 (2H, m), 1.4 (6H, m), 0.88 (3H, m).
MS: m/e=375, 258, 230, 225, 174, 173, 141, 129, 128, 115, 91.

(48) 3-Carboxymethyl-5-(2-phenylcinnamylidene)rhodanine
Yield: 34%.
Melting Point: 246°–249° C. (ethyl acetate-isopropyl ether).
NMR: $\delta$=7.8–6.9 (12H, m), 4.46 (2H, s).
MS: m/e=381, 264, 236, 235, 234, 231, 203, 202.

(49) 3-Carboxymethyl-5-(2-bromocinnamylidene)rhodanine
Yield: 62%.
Melting Point: 241°–244° C. (acetic acid-water).
NMR: $\delta$=8.16 (1H, s), 7.85 (3H, m), 7.5 (3H, m), 4.73 (2H, s).
MS: m/e=385, 304, 258, 240, 238, 187, 159, 115.

(50) 3-Carboxymethyl-5-(2-chlorocinnamylidene)rhodanine
Yield: 74%.
Melting Point: 263°–266° C.
NMR: $\delta$=7.9–7.7 (4H, m), 7.6–7.4 (3H, m), 4.72 (2H, s).
MS: m/e=401, 399, 194, 159, 115.

(51) 3-Carboxymethyl-5-(3-methylcinnamylidene)rhodanine
Yield: 60%.
Melting Point: 220°–226° C. (ethanol-water).
NMR: $\delta$=7.8–7.6 (3H, m), 7.5–7.3 (3H, m), 6.60 (1H, wide s), 4.70 (2H, s), 2,38 (3H, wide s).
MS: m/e=319, 273, 174, 173, 169, 141, 115.

(52) 3-Carboxymethyl-5-(3-propylcinnamylidene)rhodanine
Yield: 89%.
NMR: $\delta$=7.9–7.0 (6H, m), 6.53 & 6.37 (1H, each d), 4.73 & 4.66 (2H, each s), 2.88 & 2.64 (2H, each m), 1.4 (2H, m), 0.9 (3H, m).
MS: m/e=347, 202, 197, 173, 160, 153, 141, 129, 128, 115.

(53) 3-Carboxymethyl-5-(3-phenylcinnamylidene)rhodanine
Yield: 85%.
Melting Point: 232°–237° C. (acetic acid-water).
NMR: $\delta$=7.6–7.2 (10H, m), 7.15 (1H, d), 6.93 (1H, d), 4.66 (2H, s).
MS: m/e=381, 336, 264, 236, 235, 231, 203, 202.

(54) 3-Carboxymethyl-5-(2,3-dimethylcinnamylidene)rhodanine
Yield: 67%.
NMR: $\delta$=7.93 (0.4H, s), 7.5–7.1 (5.6H, m), 4.74 & 4.64 (2H, each s), 2.3–1.8 (6H, m).
MS: m/e=333, 188, 183, 173, 155, 128, 115.

Example 2

3-Carboethoxymethyl-5-benzylidenerhodanine

Under an atmosphere of nitrogen, 4.2 ml of anhydrous N,N-dimethylformamide was added dropwise to 0.279 g of 3-carboxymethyl-5-benzylidenerhodanine (prepared as described in Example 1) at room temperature, and then 1.14 ml of methanol solution of 91.15 mg of tetramethylammonium hydroxide was added dropwise. After the mixture was stirred at room temperature for 20–30 minutes, 0.075 ml of ethyl brimide was added dropwise to the reaction mixture. The mixture was stirred at the same temperature for about 2 hours, and then concentrated under reduced pressure. The residue was diluted with 15 ml of water and extracted with ethyl acetate. The extract was washed with 50 ml of aqueous solution of sodium bicarbonate, 50 ml of water and 50 ml of aqueous solution of sodium chloride, dried over magnesium sulfate, and concentrated under reduced pressure. The residue was recrystallized from a mixture of ethyl acetate and n-hexane (1:3) to obtain 14 mg of the titled compound.
Melting Point: 122°–125° C. (ethyl acetate-n-hexane).
TLC (cyclohexane:ethyl acetate=2:1): Rf=0.64.
NMR (CDCl$_3$ solution): $\delta$=7.65 (1H, s), 7.38 (5H, s), 4.78 (2H, s), 4.18 (2H, q), 1.26 (3H, t).
MS: m/e=307, 135, 134, 91, 90, 89, 72.

In the same manner, the following compound was obtained.

(1) 3-Carbobenzyloxymethyl-5-benzylidenerhodanine
Yield: 1%.
Melting Point: 156°–159° C. (n-hexane-ethyl acetate).
TLC (cyclohexane:ethyl acetate=2:1): Rf=0.60.
MS: m/e=369, 263, 134, 91, 72.

Example 3

(E,E)-3-Carboxymethyl-5-(2-methylcinnamylidene)rhodanine N-methyl-D-glucamine salt To a solution of 2.001 g of N-methyl-D-glucamine in 20 ml of water was added 3.194 g of 3-carboxymethyl-5-(2-methylcinnamylidene)-rhodanine [prepared as described in Example 1 (35)], and the mixture was heated to dissolve the rhodanine derivative, and then 40 ml of methanol was added to the solution at the same temperature. The mixture was cooled to room temperature and the precipitated crystals were filtered. The resulting crystals were washed with 5 ml of mixture of water and methanol (1:2), and 5 ml of methanol, and dried under reduced pressure to obtain 3.73 g of the titled compound.
Melting Point: 163°–165° C.
NMR: $\delta$=7.7–7.1 (7H, m), 4.4 (2H, m), 3.9 (1H, m), 3.66 (1H, wide d), 3.48 (4H, m), 3.0 (2H, m), 2.51 (3H, s), 2.22 (3H, s).
Infrared absoption spectrum (KBr tablet method): $\nu$=3400, 1704, 1606, 1572, 1325, 1190 cm$^{-1}$.

Example 4

1000 tablets for oral administration each containing 50 mg of an active ingredient per tablet were prepared from the following compounds according to a known process.

| | |
|---|---|
| ● 3-Carboxymethyl-5-benzylidenerhodanine | 50 g |
| ● Sodium citrate | 25 g |
| ● Alginic acid | 10 g |
| ● Polyvinyl pyrrolidone | 10 g |
| ● Magnesium stearate | 5 g |

In the same manner, 1000 tablets for oral administration each containing 50 mg of an active ingredient were obtained using the compound of Example 1(11), 1(14), 1(18), 1(19), 1(22), 1(28), 1(29), 1(30), 1(32), 1(33), 1(35), 1(41), 1(43), 1(45), 1(47), 1(49), 1(51), 1(53) or 1(54) or Example 3.

I claim:
1. A rhodanine derivative represented by the general formula:

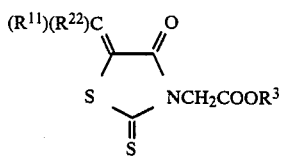

wherein
R[11] represents a hydrogen atom;
R[22] represents:
(1) a 5- to 10-membered mono or bicyclic heterocyclic group containing one of nitrogen, oxygen and sulfur atoms which is substituted by at least one member selected from the group consisting of
(b) trifluoromethyl group,
(e) carboxyl group,
(f) amino group which may be substituted by alkyl group(s) of 1-4 carbon atoms,
(g-3) alkoxy group of 1-5 carbon atoms, and
(j) alkyl group of 1-4 carbon atoms which is substituted by at least one of:
(c) hydroxyl group, and
(i) 5- to 10-membered mono or bicyclic heterocyclic group containing one or two nitrogen, oxygen and sulfur atoms which is unsubstituted or substituted by at least one member selected from the group consisting of
(a) halogen atom,
(d) nitro group,
(g) alkyl, alkoxy or alkylthio group of 1-5 carbon atoms and
one member selected from the group consisting of the above-described substituents (b), (c), (e), (f) and (h), or
(2)

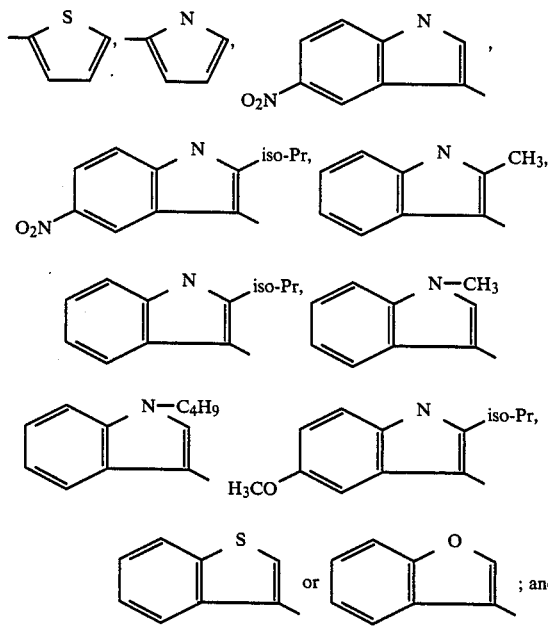

R[3] represents a hydrogen atom, an alkyl group of 1-12 carbon atoms, an aralkyl group of 7-13 carbon atoms, a cycloalkyl or cycloalkenyl group of 7-13 carbon atoms, a cycloalkyl or cycloalkenyl group of 4-7 carbon atoms which is unsubstituted or substituted by at least one alkyl group of 1-4 carbon atoms, or a phenyl group which is unsubstituted or substituted by at least one member selected from the group consisting of the above-described substituents (a), (b), (c), (d), (e), (f), (g), (h), (i) and (j) or, when R[3] represents a hydrogen atom, non-toxic salts of the acids.

2. A rhodanine derivative as described in claim 1, wherein R[3] is a hydrogen atom or an alkyl group of 1-12 carbon atoms, or when R[3] represents a hydrogen atom, a non-toxic salt of the acid.

3. A rhodanine derivative as described in claim 1, wherein R[11] represents a hydrogen atom and R[22] is a 2-thienyl, 5-hydroxymethyl-2-furyl, 2-pyrrolyl, 5-methoxy-3-indolyl, 2-isopropyl-5-methoxy-3-indolyl, 5-nitro-3-indolyl, 5-carboxy-3-indolyl, 1-methyl-3-indolyl, 2-methyl-3-indolyl, 2-isopropyl-3-indolyl, 3-benzo[b]furyl, 3-benzo[b]thienyl, 5-(3-pyridylmethyl)-2-thienyl, 1-butyl-3-indolyl, 1-benzyl-3-indolyl or 2-isopropyl-5-nitro-3-indolyl group or a non-toxic salt of the acid when R[3] represents a hydrogen atom.

4. A compound as described in claim 1, which is 3-carboxymethyl-5-(2-thienylmethylene)rhodanine.

5. A compound as described in claim 1, which is 3-carboxymethyl-5-(5-methoxy-3-indolylmethylene)rhodanine.

6. A compound as described in claim 1, which is 3-carboxymethyl-5-(2-methyl-3-indolylmethylene)rhodanine.

7. A compound as described in claim 1, which is 3-carboxymethyl-5-(2-isopropyl-3-indolylmethylene)rhodanine.

8. A compound as described in claim 1, which is 3-carboxymethyl-5-(1-methyl-3-indolylmethylene)rhodanine.

9. A compound as described in claim 1, which is 3-carboxymethyl-5-(5-nitro-3-indolylmethylene)rhodanine.

10. A compound as described in claim 1, which is 3-carboxymethyl-5-[5-(3-pyridylmethyl)-2-thienylmethylene]-rhodanine.

11. A compound as described in claim 1, which is 3-carboxymethyl-5-(2-pyrrolylmethylene)rhodanine.

12. A compound as described in claim 1, which is 3-carboxymethyl-5-(5-hydroxymethyl-2-furylmethylene)rhodanine.

13. A compound as described in claim 1, which is 3-carboxymethyl-5-(2-isopropyl-5-methoxy-3-indolylmethylene)rhodanine.

14. A compound as described in claim 1, which is 3-carboxymethyl-5-(1-butyl-3-indolylmethylene)rhodanine.

15. A compound as described in claim 1, which is 3-carboxymethyl-5-(1-benzyl-3-indolylmethylene)rhodanine.

16. A compound as described in claim 1, which is 3-carboxymethyl-5-(2-isopropyl-5-nitro-3-indolylmethylene)rhodanine.

17. A method of preventing or treating nerve disturbances, retinopathy, diabetic cataract or renal disorders caused by an aldose reductase in mammals which comprises administering a therapeutically effective amount of at least one rhodanine derivative represented by the general formula:

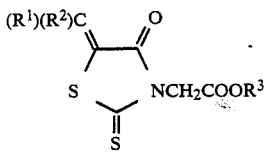 (I)

wherein
$R^1$ represents a hydrogen atom;
$R^2$ represents a 5- to 10-membered mono or bicyclic heterocyclic group containing one or two nitrogen, oxygen and sulfur atoms which is unsubstituted or substituted by at least one member selected from the group consisting of: oxo group,
(a) halogen atom,
(b) trifluoromethyl group,
(c) hydroxy group,
(d) nitro group,
(e) carboxyl group,
(f) amino group which may be substituted by alkyl group(s) of 1-4 carbon atoms,
(g) alkyl, alkoxy or alkylthio group of 1-5 carbon atoms,
(h) phenyl group, and
(j) alkyl group of 1-4 carbon atoms which is substituted by at least one member selected from the group consisting of:
one of the above-described substituents (c) and (h), and
(k) 5- to 10-membered mono or bicyclic heterocyclic group containing one or two nitrogen, oxygen and sulfur atoms which is unsubstituted or substituted by at least one of the above-described substituents (a) to (h); and $R^3$ represents a hydrogen atom, an alkyl group of 1-12 carbon atoms, an aralkyl group of 7-13 carbon atoms, a cycloalkyl or cycloalkenyl group of 4-7 carbon atoms which is unsubstituted or substituted by at least one alkyl group of 1-4 carbon atoms, or a phenyl group which is unsubstituted or substituted by at least one of the above-described substituents (a) to (j), or when $R^3$ represents a hydrogen atom, non-toxic salts of the acids.

* * * * *

UNITED STATES PATENT AND TRADEMARK OFFICE
CERTIFICATE OF CORRECTION

PATENT NO. : 4,831,045
DATED : May 16, 1989
INVENTOR(S) : Tadao Tanouchi et al

It is certified that error appears in the above-identified patent and that said Letters Patent is hereby corrected as shown below:

<u>IN THE CLAIMS</u>:

Claim 1, (column 17, lines 66-67), delete "a cycloalkyl or cycloalkenyl group of 7-13 carbon atoms,".

Signed and Sealed this

Sixth Day of March, 1990

*Attest:*

JEFFREY M. SAMUELS

*Attesting Officer*   *Acting Commissioner of Patents and Trademarks*